United States Patent
Liu et al.

(10) Patent No.: US 10,926,110 B2
(45) Date of Patent: Feb. 23, 2021

(54) BEAM DIAGNOSTIC SYSTEM FOR NEUTRON CAPTURE THERAPY SYSTEM

(71) Applicant: NEUBORON MEDTECH LTD., Jiangsu (CN)

(72) Inventors: Yuanhao Liu, Jiangsu (CN); Weilin Chen, Jiangsu (CN)

(73) Assignee: NEUBORON MEDTECH LTD., Jiangsu (CN)

(*) Notice: Subject to any disclaimer, the term of this patent is extended or adjusted under 35 U.S.C. 154(b) by 372 days.

(21) Appl. No.: 15/894,043

(22) Filed: Feb. 12, 2018

(65) Prior Publication Data

US 2018/0169440 A1    Jun. 21, 2018

Related U.S. Application Data

(63) Continuation of application No. PCT/CN2016/090273, filed on Jul. 18, 2016.

(30) Foreign Application Priority Data

Sep. 28, 2015  (CN) .......................... 201510629791.9
Sep. 28, 2015  (CN) .......................... 201520759359.7

(51) Int. Cl.
*A61N 5/10* (2006.01)
*G01T 3/06* (2006.01)
*A61N 5/00* (2006.01)

(52) U.S. Cl.
CPC ............. *A61N 5/1075* (2013.01); *A61N 5/10* (2013.01); *A61N 5/1048* (2013.01);
(Continued)

(58) Field of Classification Search
CPC ........ A61N 2005/005; A61N 2005/109; A61N 5/1075; A61N 5/1077
See application file for complete search history.

(56) References Cited

U.S. PATENT DOCUMENTS 4,666,651 A * 5/1987 Barjon .................... A61N 5/10
                                                                376/108
5,392,319 A    2/1995 Eggers
(Continued)

FOREIGN PATENT DOCUMENTS

CN    101820356 A    9/2010
CN    102946944 A    2/2013
(Continued)

OTHER PUBLICATIONS

International Search Report of PCT/CN2016/090273, dated Sep. 21, 2016.

*Primary Examiner* — Christine H Matthews
(74) *Attorney, Agent, or Firm* — Locke Lord LLP; Tim Tingkang Xia, Esq.

(57) ABSTRACT

Provided is a beam diagnostic system for a neutron capture therapy system. The neutron capture therapy system includes a charged particle beam, a charged particle beam inlet for passing the charged particle beam, a neutron generating unit generating a neutron beam by a nuclear reaction with the charged particle beam, and a beam shaping assembly for adjusting flux and quality of the neutron beam generated by the neutron generating unit and a beam outlet adjoining to the beam shaping assembly. The charged particle beam inlet is accommodated into the beam shaping assembly and the neutron generating unit is accommodated in the beam shaping assembly. The beam diagnostic system includes a charged particle beam diagnostic device and a neutron beam diagnostic device, and the beam diagnostic system is used to simultaneously diagnose whether the neutron capture therapy system and/or the beam diagnostic system is malfunctioning.

20 Claims, 2 Drawing Sheets

(52) U.S. Cl.
CPC ......... *A61N 5/1049* (2013.01); *A61N 5/1077* (2013.01); *A61N 2005/005* (2013.01); *A61N 2005/109* (2013.01); *G01T 3/06* (2013.01)

(56) References Cited

U.S. PATENT DOCUMENTS

2007/0041499 A1\* 2/2007 Lu .......................... A61N 5/103
378/65
2011/0257457 A1 10/2011 Graf et al.
2012/0294423 A1 11/2012 Cheung et al.

FOREIGN PATENT DOCUMENTS

| | | |
|---|---|---|
| CN | 205073541 U | 3/2016 |
| EP | 0313716 A1 | 5/1989 |
| EP | 2189632 A1 | 5/2010 |
| EP | 2979728 A1 | 2/2016 |
| JP | 481615 | 3/1992 |
| JP | 2002135917 A | 5/2002 |
| JP | 2008022920 A | 2/2008 |
| JP | 2010107376 A | 5/2010 |
| JP | WO2012014671 A1 | 9/2013 |
| JP | 2014226331 A | 12/2014 |
| RU | 2007132466 A | 3/2009 |
| TW | 201438788 A | 10/2014 |
| WO | 2007093965 A1 | 8/2007 |

\* cited by examiner

BEAM DIAGNOSTIC SYSTEM FOR NEUTRON CAPTURE THERAPY SYSTEM

RELATED APPLICATION INFORMATION

This application is a continuation of International Application No. PCT/CN2016/090273, filed on Jul. 18, 2016, which claims priority to Chinese Patent Application No. 201510629791.9, filed on Sep. 28, 2015 and Chinese Patent Application No. 201520759359.7, filed on Sep. 28, 2015, the disclosures of which are hereby incorporated by reference.

FIELD OF THE DISCLOSURE

The present disclosure relates generally to a beam diagnostic system, and, more particularly, to a beam diagnostic system for neutron capture therapy system.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Figure 1:
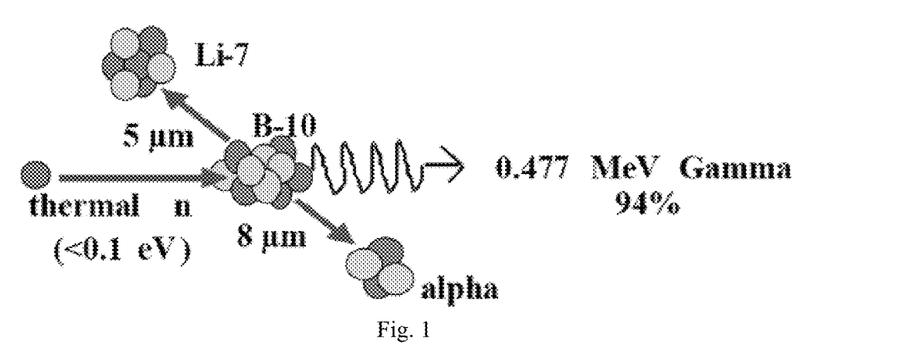
FIG. 1 is a schematic view of boron neutron capture reaction.
Figure 2:
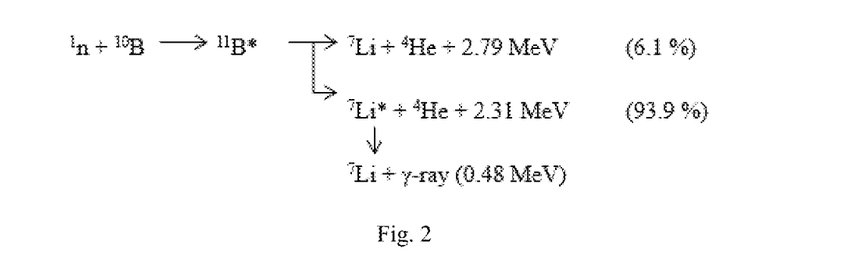
FIG. 2 is a nuclear reaction formula of $^{10}B$ $(n,\alpha)^7Li$ neutron capture.

BNCT takes advantage that the boron ($^{10}$B)-containing pharmaceuticals have high neutron capture cross section and produces $^4$He and $^7$Li heavy charged particles through $^{10}$B(n,α)$^7$Li neutron capture and nuclear fission reaction. As illustrated in FIGS. 1 and 2, a schematic drawing of BNCT and a nuclear reaction formula of $^{10}$B (n,α)$^7$Li neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

Beam detection and diagnosis which directly relates to the dose and effect of an irradiation therapy, belongs to an important subject in a neutron capture therapy system. As disclosed in the prior art, in a neutron capture therapy system, the dose of a neutron beam during irradiation is measured, for example, by attaching a gold wire for measuring a neutron beam to an irradiation object in advance, detaching the gold wire therefrom during the irradiation with a neutron beam, and measuring an amount of activated gold of the gold wire. It is intended to control (for example, stop) the neutron capture therapy system so as to irradiate the irradiation object with the neutron beam with a desired dose on the basis of the measured dose.

However, in this case, for example, when a dose rate of a neutron beam varies for some reasons after measuring the amount of activated gold of the gold wire, it may not be possible to cope with this variation and it may thus be difficult to irradiate an irradiation object with a neutron beam with a desired dose. That is to say, in the aforementioned neutron capture therapy system, the irradiation dose of the radiation cannot be detected in real time, and it cannot be diagnosed whether all components of the neutron capture therapy system and detection devices are malfunctioning.

Accordingly, it is necessary to provide a neutron capture therapy system capable of improving the accuracy of a neutron beam irradiation dose and a beam diagnostic system capable of performing fault diagnosis.

The statements in this section merely provide background information related to the present disclosure and may not constitute prior art.

SUMMARY

One aspect of the present disclosure is to improve the accuracy of a neutron beam irradiation dose for a neutron capture therapy system and to provide a beam diagnostic system which can be used in a neutron capture therapy system to perform fault diagnosis. Provided in one technical scheme is a beam diagnostic system for a neutron capture therapy system. Wherein the neutron capture therapy system includes a charged particle beam, a charged particle beam inlet for passing the charged particle beam, a neutron generating unit generating a neutron beam by means of a nuclear reaction with the charged particle beam, and a beam shaping assembly for adjusting flux and quality of the neutron beam generated by the neutron generating unit and a beam outlet adjoining to the beam shaping assembly, wherein the charged particle beam inlet is accommodated into the beam shaping assembly and the neutron generating unit is accommodated in the beam shaping assembly, the beam diagnostic system includes a charged particle beam diagnostic device and a neutron beam diagnostic device, and the beam diagnostic system is used to simultaneously diagnose whether the neutron capture therapy system and/or the beam diagnostic system is malfunctioning. The beam diagnostic system improves the accuracy of a neutron beam irradiation dose by detecting a charged particle beam and a neutron beam simultaneously. In addition, the beam diagnostic system is used for judging which devices and/or components in the neutron capture therapy system are abnormal by means of a series of detection results, or judging whether a detection device in the beam diagnostic system is abnormal. Thus, not only the accuracy of the neutron beam irradiation dose is improved with a purpose, but also the maintenance time and cost are greatly reduced.

Implementations of this aspect may include one or more of the following features.

Preferably, the neutron capture therapy system further includes a cooling device arranged into the neutron beam generating unit for cooling the neutron beam generating unit, and the beam diagnostic system further includes a temperature detection device for detecting the temperature of the cooling device so as to obtain a situation of the neutron beam generated by the neutron generating unit and a displacement detection device for diagnosing whether the irradiated body displaces. By means of such setting, various detection devices are disposed from the source of an accelerator to the terminal of the irradiated body. The detection devices are used for judging whether each key component of the neutron capture therapy system or the detection devices themselves are abnormal. More particularly, the detection devices are disposed from the source of the accelerator to the terminal of the irradiated body in such a way that a detection device is disposed at a vacuum tube at the source of the accelerator, a detection device is disposed at the neutron generating unit, a detection device is disposed at the cooling device which adjoins to the neutron generating unit and is used for cooling the neutron generating unit, a detection device is disposed in the beam shaping assembly, a detection device is disposed at the beam outlet, and a detection device is disposed at the irradiated body.

More particularly, the neutron capture therapy system further includes a beam expanding device for expanding the charged particle beam; the charged particle beam diagnostic device further includes a first current detection device for detecting the intensity and stability of the charged particle beam before entering the charged particle beam inlet and a second current detection device for detecting the intensity and change situation of the charged particle beam interacting with the neutron generating unit; and the neutron beam diagnostic device further includes a first neutron beam monitoring device which is used for detecting the intensity change and space distribution of the neutron beam in the beam shaping assembly and is embedded into the beam shaping assembly, and a second neutron beam monitoring device which is used for detecting the intensity change and space distribution of the neutron beam at the beam outlet and is embedded at the beam outlet.

More preferably, the first current detection device is a Faraday cup electrometer, which is a cup-shaped metal vacuum detector for measuring the incident intensity and stability of the charged particle beam, wherein a measured current may be used for determining the quantity of the charged particles. When the charged particle beam enters the Faraday cup electrometer, a current will be generated. A successive charged particle beam with a single charge is calculated by means of FORMULA 1, where N represents the quantity of charged particles, t represents time (in second), I represents a measured current (in ampere), and e represents an elementary charge (about $1.60 \times 10^{-19}$ coulombs). It is estimable that if the measured current is $10^{-9}$ A (1 nA), about six billion charged particles are collected by the Faraday cup electrometer.

$$\frac{N}{t} = \frac{I}{e} \qquad \text{(FORMULA 1)}$$

Certainly, it is well known to a person skilled in the art that the first current detection device 100 may be any detection device suitable for measuring the incident intensity and stability of the charged particle beam at the vacuum tube of the accelerator, such as a wall current monitor and a beam current transformer.

The wall current monitor bridges sampling resistors to two ends of a ceramic isolation segment, a voltage sampling signal can be obtained when a beam mirror current flows through the sampling resistors, and the voltage sampling signal is calculated by means of FORMULA 2, where V represents a detected voltage value, $I_b$ represents a charged particle beam current, Z may be equivalent to resistance under a specific frequency, and a wall current monitor equivalent circuit is a parallel RLC circuit, as shown in FORMULA 3. Therefore, the current of the charged particle beam within a certain period of time t can be calculated according to the detected voltage value.

$$V = -I_b(t)\, Z \qquad \text{(FORMULA 2)}$$

$$\frac{1}{Z} = \frac{1}{R} + \frac{1}{j\omega L} + j\omega C \qquad \text{(FORMULA 3)}$$

The beam current transformer is used for coupling a current signal by utilizing a secondary winding on a magnetic core to obtain the current of an original charged particle beam by analyzing the signal. The beam current transformer includes an AC Current Transformer (ACCT), a Fast Current Transformer (FCT), a Tuned Current Transformer (TCT), an Integrated Current Transformer (ICT) and a DC Current Transformer (DCCT). Due to numerous varieties, the beam current transformers will not be enumerated one by one hereinafter. Only the DCCT is taken as the beam current transformer. The DCCT modulates a DC signal to be detected to secondary harmonics of an excitation signal for detection by adopting a nonlinear magnetic modulation component.

In the present embodiment, the second current detection device 200 is a galvanometer, one end being electrically connected to the neutron generating unit T and the other one being grounded, so as to form a detection loop, thereby obtaining a current on the neutron generating unit T when the charged particle beam P bombards the neutron generating unit T. The galvanometer is made according to a principle that a current-carrying coil deflects in a magnetic field under the action of a moment of force. A coil in a common electric meter is placed on a bearing, keeps balanced by using a balance spring, and the deflection is indicated by a pointer. The bearing is frictional, so the measured current cannot be too weak. The galvanometer is suspended in the magnetic field by using a very thin metal suspension wire instead of the bearing. The suspension wire is thin and long, and a resisting moment is small, so the coil can be obviously deflected when a very weak current passes through the coil. Thus, the galvanometer is more sensitive than a common ampere meter, and can measure a micro-current ($10^{-7}$-$10^{-10}$ A) or a micro-voltage ($10^{-3}$-$10^{-6}$V) such as a light current, a physiological current and a thermal electromotive force. The first record about a nerve action potential was made by using this type of instrument.

Certainly, it is well known to a person skilled in the art that the second current detection device 200 may be any detection device suitable for detecting, near the neutron generating unit, the intensity and change situations of the charged particle beam interacting with the neutron generating unit, such as an ampere meter and a voltmeter.

In the present embodiment, the temperature detection device 300 is a thermocouple. Both ends of two conductors (referred to as thermocouple wires or thermal electrodes) with different components are connected into a loop. When the temperatures of junctions are different, an electromotive force will be generated in the loop, the phenomenon is referred to as a thermo-electric effect, the electromotive force is referred to as a thermal electromotive force. The thermocouple performs temperature measurement by utilizing the principle, wherein an end directly used for measuring a medium temperature is referred to as a working end (or measurement end) whilst the other end is referred to as a cold end (or compensation end). The cold end is connected with a display instrument or an auxiliary instrument, and the display instrument will indicate the thermal electromotive force generated by the thermocouple.

Certainly, it is well known to a person skilled in the art that the temperature detection device 300 may be any detection device suitable for being disposed in the cooling device or near the cooling device and used for detecting the temperature of the cooling device so as to obtain a situation of the neutron beam generated by the neutron generating unit, such as a resistance thermometer, which measures a temperature according to a rule of varying of conductor resistance along with temperature by using a temperature sensor made of a material characterized by varying of given resistance along with temperature.

A common neutron beam monitoring device for real-time detection may have two different detection principles, namely an ionization chamber and a scintillator detector, can be realized. Those adopting ionization chamber structures as substrates include an He-3 proportional counter, a $BF_3$ proportional counter, a fission chamber and a boron ionization chamber. The scintillator detector may be divided into organic and inorganic materials, and for the purpose of detecting thermal neutrons, the scintillator detector mainly adds high thermal neutron capture section elements such as Li or B. In short, most of neutron energies detected by this type of detectors are the thermal neutrons, which are all heavy charged particles and nuclear fission fragments released by means of a capture or nuclear fission reaction between elements and neutrons, a great number of ion pairs are generated in the ionization chamber or the scintillator detector, and after the charges are collected, a current signal may be converted into a voltage pulse signal via appropriate circuit conversion. A neutron signal and a γ signal can be easily distinguished from each other by analyzing the magnitude of a voltage pulse. In a high-intensity neutron field such as a BNCT, the gas pressure of the ionization chamber, the concentration of coating of fissionable materials or boron or the concentration of the high neutron capture section elements in the scintillator detector can be appropriately reduced, so the sensitivity to neutrons can be effectively reduced, and the situation of signal saturation is avoided.

More preferably, the first neutron beam monitoring device 400 is a fission chamber. When passing through the fission chamber, a neutron beam ionizes gas molecules inside the fission chamber or a wall portion of the fission chamber to generate an electron and an ion with a positive charge, the electron and the positive charge ion are referred to as the aforementioned ion pair. The fission chamber internally has an external electric field high voltage, so the electron moves toward a central anode wire, and the positive charge ion moves toward a surrounding cathode wall, thus generating an electronic pulse signal which can be measured. An energy needed for generating an ion pair by gas molecules is referred to as an average ionizing energy, the value varying with a gas type. For example, the average ionizing energy of air is about 34 eV. If a neutron beam of 340 keV exists, the air will generate about 10 k ion pairs.

Certainly, it is well known to a person skilled in the art that the first neutron beam monitoring device 400 may be any detection device suitable for being embedded in the beam shaping assembly and used for detecting the intensity change and space distribution of a neutron beam in the beam shaping assembly such as an He-3 proportional counter, a BF3 proportional counter, a boron ionization chamber and a scintillator detector.

More preferably, the second neutron beam monitoring device 500 is a scintillator detector, and after certain materials absorb energy, visible light will be emitted, and the materials are referred to as scintillating materials. It utilizes ionizing radiation to excite an electron in a crystal or molecule to an exciting state, fluorescent light emitted when the electron returns to a base state is used for monitoring a neutron beam after being collected. The visible light emitted after the scintillator detector interacts with the neutron beam can be converted into an electron by utilizing a photomultiplier, and the electron is multiplied and amplified, wherein the multiplication and amplification rate of the electron can reach 107 to 108 usually. The quantity of electrons output from an anode is in direct proportion to energy of an incident neutron beam, and therefore the scintillator detector can measure the energy of the neutron beam.

Certainly, it is well known to a person skilled in the art that the second neutron beam monitoring device 500 may be any detection device suitable for being disposed in the beam exit or near the beam exit and used for detecting the intensity change and space distribution of a neutron beam at the beam exit such as an He-3 proportional counter, a $BF_3$ proportional counter, a boron ionization chamber and a fission chamber.

More preferably, the displacement detection device 600 is an infrared signal detector, the infrared detector works by detecting an infrared ray emitted by a human body. The detector collects external infrared radiation and further gathers the external infrared radiation to an infrared sensor. The infrared sensor usually adopts a pyroelectric element. The element will release a charge outward after receiving an infrared radiation temperature change, and will give an alarm after detection. The detector aims to detect human body radiation. A radiation-sensitive element must be very sensitive to infrared radiation of which a wavelength is about 10 μm.

Certainly, it is well known to a person skilled in the art that the displacement detection device 600 may be any detection device suitable for being used for detecting the displacement change of the irradiated body, such as a displacement sensor. The displacement sensor determines whether the irradiated body moves according to the displacement change of the irradiated body relative to a certain reference substance. It is also well known to a person skilled in the art that the displacement detection device not only can be used for detecting the displacement change of the irradiated body, but also can be used for detecting the displacement change of a supporting piece for fixing the irradiated body and/or a treatment table, thereby indirectly knowing the displacement change of the irradiated body.

It is well known to a person skilled in the art that the number of first current detection devices, the number of second current detection devices, the number of temperature detection devices, the number of first neutron beam monitoring devices, the number of second neutron beam monitoring devices, the number of displacement detection devices, and detection elements are not limited to this.

According to a function relationship between detection results of detection and/or monitoring devices, malfunctioning components can be obviously enumerated. Several fault diagnosis situations made according to corresponding detection results will be enumerated hereinafter.

When it is detected that any one detection or monitoring device of the first current detection device, the second current detection device, the temperature detection device, the first neutron beam monitoring device and the second neutron beam monitoring device is abnormal whilst all other detection or monitoring devices are normal, it is concluded that the abnormal detection or monitoring device is malfunctioning; and when it is detected that the displacement detection device is abnormal whilst all other detection or monitoring devices are normal, it is concluded that the displacement of the irradiated body is changed or the displacement detection device is malfunctioning.

More particularly, the neutron capture therapy system further includes an accelerator for accelerating the charged particle beam, and when it is detected that the first current detection device, the second current detection device, the temperature detection device, the first neutron beam monitoring device and the second neutron beam monitoring device are all abnormal, it is concluded that the accelerator is malfunctioning.

When it is detected that the second current detection device, the temperature detection device, the first neutron beam monitoring device and the second neutron beam monitoring device are all abnormal whilst both the first current detection device and the displacement detection device are normal, it is concluded that the beam expanding device is malfunctioning.

When it is detected that the temperature detection device, the first neutron beam monitoring device and the second neutron beam monitoring device are all abnormal whilst the first current detection device, the second current detection device and the displacement detection device are all normal, it is concluded that the neutron generating unit and/or the cooling device is malfunctioning.

When it is detected that both the first neutron beam monitoring device and the second neutron beam monitoring device are abnormal whilst the first current detection device, the second current detection device, the temperature detection device and the displacement detection device are all normal, it is concluded that the beam shaping assembly is malfunctioning.

More particularly, the first neutron beam monitoring device includes a first neutron beam monitoring member and a second neutron beam monitoring member which are located at two opposite sides in the beam shaping assembly respectively, the second neutron beam monitoring device includes a third neutron beam monitoring member and a fourth neutron beam monitoring member which are located at two opposite sides of the beam outlet respectively, and when it is detected that any one of monitoring results of the first neutron beam monitoring member and the second neutron beam monitoring member and/or any one of the third neutron beam monitoring member and the fourth neutron beam monitoring member is abnormal, it is concluded that the abnormal neutron beam monitoring member is malfunctioning or the uniformity of the neutron beam is abnormal.

Certainly, it is well known to a person skilled in the art that the aforementioned fault diagnosis situations made according to the detection results are only some enumerated common situations, there are many permutations and combinations, and the above modes can be still adopted to judge which the neutron capture therapy system or detection devices are malfunctioning and which faults are included. Here, although they are not enumerated one by one, changes made according to such a spirit still fall within the summary of the present disclosure.

More preferably, the beam diagnostic system includes a control device with a control unit, wherein the control unit sends a human-perceivable signal according to a detection result of the beam diagnostic system so as to confirm a next operation of the neutron capture therapy system. The human-perceivable signal may be a signal which can be perceived by human functional organs such as auditory sense, visual sense, tactile sense or smell sense. For example, the signal is one or more forms in various signals such as a sound-making alarm, an alarm lamp, a vibrating signal and a pungent smell emitting signal. Preferably, the control device further includes a display portion, the display portion is used for displaying a detection result of the detection device and/or a fault diagnosis situation made according to the detection result on display equipment, and the display equipment may be common display equipment such as a television or a liquid crystal display. According to a feedback from the control device, an operator can easily determine a malfunctioning component, thereby maintaining the neutron capture therapy system and/or the beam diagnostic system with a purpose.

In another aspect of the present disclosure, a beam diagnostic system for neutron capture therapy system improve the accuracy of a neutron beam irradiation dose for a neutron capture therapy system and perform fault diagnosis. The neutron capture therapy system includes: a charged particle beam; a charged particle beam inlet for passing the charged particle beam; a neutron beam generating unit for generating the neutron beam by means of a nuclear reaction with the charged particle beam; a beam shaping assembly for adjusting flux and quality of the neutron beam generated by the neutron beam generating unit; and a beam outlet adjoining to the beam shaping assembly, wherein the beam diagnostic system which includes a charged particle beam diagnostic device and a neutron beam diagnostic device is used to simultaneously diagnose whether the neutron capture therapy system and/or the beam diagnostic system is malfunctioning; wherein the neutron beam diagnostic device further includes a first neutron beam monitoring device which is used for detecting the intensity change and space distribution of the neutron beam in the beam shaping assembly and is embedded into the beam shaping assembly, and a second neutron beam monitoring device which is used for detecting the intensity change and space distribution of the neutron beam at the beam outlet and is embedded at the beam outlet; and wherein the charged particle beam diagnostic device, the first neutron beam monitoring device and the second neutron beam monitoring device is used to simultaneously diagnose whether the neutron capture therapy system and/or the beam diagnostic system is malfunctioning.

More particularly, the neutron capture therapy system further includes a cooling device arranged into the neutron beam generating unit for cooling the neutron beam generating unit, and the beam diagnostic system further includes a temperature detection device for detecting the temperature of the cooling device so as to obtain a situation of the neutron beam generated by the neutron generating unit and a displacement detection device for diagnosing whether the irradiated body displaces.

More particularly, the neutron capture therapy system further includes a beam expanding device for expanding the charged particle beam.

Preferably, the charged particle beam diagnostic device further includes a first current detection device for detecting the intensity and stability of the charged particle beam before entering the charged particle beam inlet and a second current detection device for detecting the intensity and change situation of the charged particle beam interacting with the neutron generating unit.

Preferably, the beam diagnostic system includes a control device with a control unit, wherein the control unit sends a human-perceivable signal according to a detection result of the beam diagnostic system so as to confirm a next operation of the neutron capture therapy system.

In yet another aspect of the present disclosure, a beam diagnostic system for neutron capture therapy system improve the accuracy of a neutron beam irradiation dose for a neutron capture therapy system and perform fault diagnosis. The neutron capture therapy system includes: a charged particle beam; a charged particle beam inlet for passing the charged particle beam; a neutron beam generating unit for generating the neutron beam by means of a nuclear reaction with the charged particle beam; a beam shaping assembly for adjusting flux and quality of the neutron beam generated by the neutron beam generating unit; and a beam outlet adjoining to the beam shaping assembly, wherein the beam diagnostic system which includes a charged particle beam diagnostic device and a neutron beam diagnostic device is used to simultaneously diagnose whether the neutron capture therapy system and/or the beam diagnostic system is malfunctioning; wherein the charged particle beam diagnostic device further includes a first current detection device for detecting the intensity and stability of the charged particle beam before entering the charged particle beam inlet and a second current detection device for detecting the intensity and change situation of the charged particle beam interacting with the neutron generating unit; and wherein the first current detection device, the second current detection device and the neutron beam diagnostic device is used to simultaneously diagnose whether the neutron capture therapy system and/or the beam diagnostic system is malfunctioning.

More particularly, the neutron capture therapy system further includes a cooling device arranged into the neutron beam generating unit for cooling the neutron beam generating unit, and the beam diagnostic system further includes a temperature detection device for detecting the temperature of the cooling device so as to obtain a situation of the neutron beam generated by the neutron generating unit and a displacement detection device for diagnosing whether the irradiated body displaces.

More particularly, the neutron capture therapy system further includes a beam expanding device for expanding the charged particle beam.

Preferably, the neutron beam diagnostic device further includes a first neutron beam monitoring device which is used for detecting the intensity change and space distribution of the neutron beam in the beam shaping assembly and is embedded into the beam shaping assembly, and a second neutron beam monitoring device which is used for detecting the intensity change and space distribution of the neutron beam at the beam outlet and is embedded at the beam outlet.

Preferably, the beam diagnostic system includes a control device with a control unit, wherein the control unit sends a human-perceivable signal according to a detection result of the beam diagnostic system so as to confirm a next operation of the neutron capture therapy system.

Further areas of applicability will become apparent from the description provided herein. It should be understood that the description and specific examples are intended for purposes of illustration only and are not intended to limit the scope of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7Li$ $(p, n)^7Be$ and $^9Be$ $(p, n)^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7Li$ $(p, n)^7Be$ asks for more than $^9Be$ $(p, n)^9B$ does because of low melting point and poor thermal conductivity coefficient of the metal (lithium) target. In these embodiments of the present disclosure is $^7Li$ $(p, n)^7Be$.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux >$1 \times 10^9$ n/cm$^2$s
Fast neutron contamination <$2 \times 10^{-13}$ Gy-cm$^2$/n
Photon contamination <$2 \times 10^{-13}$ Gy-cm$^2$/n
Thermal to epithermal neutron flux ratio <0.05
Epithermal neutron current to flux ratio >0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$ Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$ Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is called as advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time <=30 min (proton current for accelerator is 10 mA)
2. 30.0RBE-Gy treatable depth >=7 cm
3. The maximum tumor dose>=60.0RBE-Gy
4. The maximum dose of normal brain tissue<=12.5RBE-Gy
5. The maximum skin dose<=11.0RBE-Gy Note: RBE stands for relative biological effectiveness. Since photons and neutrons express different biological effectiveness, the dose above should be multiplied with RBE of different tissues to obtain equivalent dose.

Figure 3:
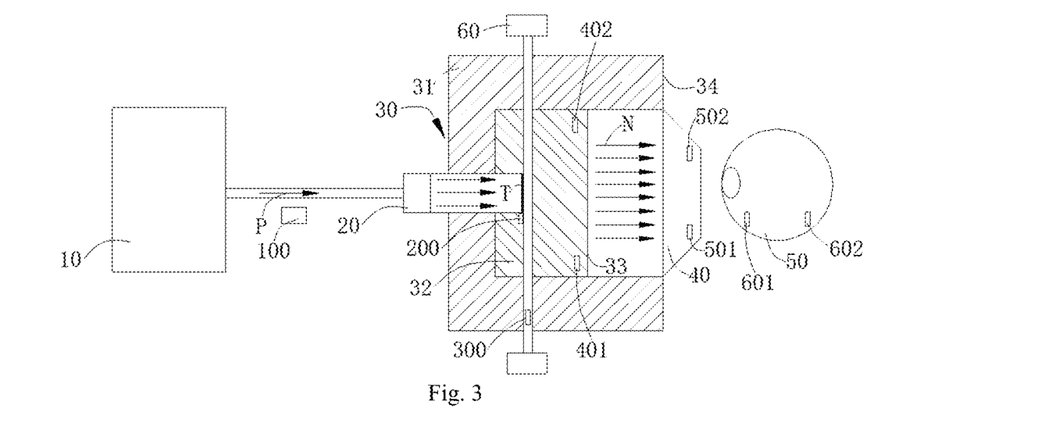
FIG. 3 is a schematic view of the beam diagnostic system for neutron capture therapy system in one embodiment of the present disclosure.
Figure 4:
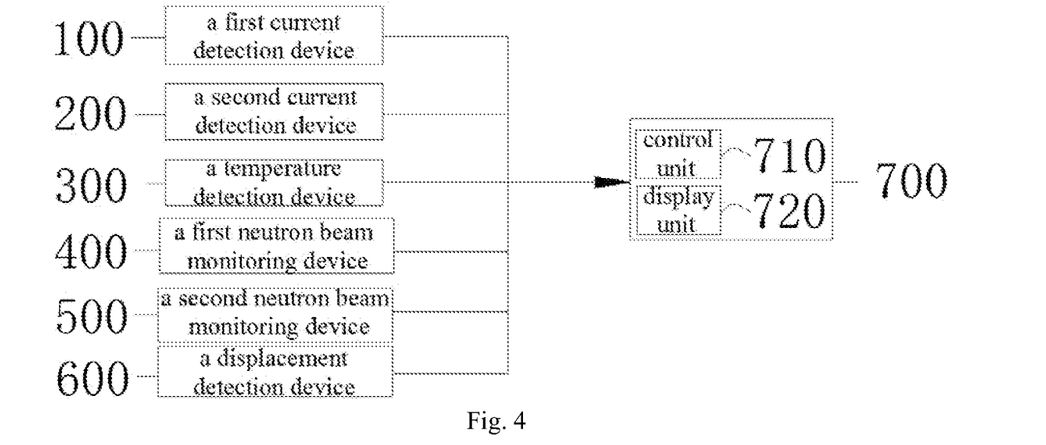
FIG. 4 is logic diagram illustrating operation of the beam diagnostic system for the neutron capture therapy system in the embodiment of the present disclosure.

Referring to FIG. 3 and FIG. 4, one aspect of the subject disclosure is to improve the accuracy of a neutron beam irradiation dose for a neutron capture therapy system and to provide a beam diagnostic system which can be used in a neutron capture therapy system to perform fault diagnosis. Provided in one embodiment is a beam diagnostic system for a neutron capture therapy system.

The neutron capture therapy system includes an accelerator 10, a beam expanding device 20, a charged particle beam inlet for passing a charged particle beam P, the charged particle beam P, a neutron beam generating unit T generating a neutron beam N by means of a nuclear reaction with the charged particle beam P, a beam shaping assembly 30 for adjusting flux and quality of the neutron beam generated by the neutron beam generating unit T, a beam outlet 40 adjoining to the beam shaping assembly 30, a irradiated body 50 irradiated by a beam emitted out from the beam outlet 40, and a cooling device 60 for putting a cooling medium at the neutron beam generating unit T to cool the neutron beam generating unit T. The accelerator 10 is used for accelerating the charged particle beam P, and may be an accelerator suitable for an accelerator-type neutron capture therapy system such as a cyclotron or a linear accelerator. The charged particle beam P here is a proton beam. The beam expanding device 20 is disposed between the accelerator 10 and the neutron beam generating unit T. The charged particle beam inlet abuts the neutron beam generating unit T and is accommodated in the beam shaping assembly 30. Three arrows between the neutron beam generating unit T and the beam expanding device as shown in FIG. 3 serve as the charged particle beam inlet. The neutron beam generating unit T is accommodated in the beam shaping assembly 30. The neutron beam generating unit T here is lithium metal. The beam shaping assembly 30 includes a reflector 31, a moderator 32 which is surrounded by the reflector 31 and abuts the neutron beam generating unit T, a thermal neutron absorber 33 abutting the moderator 32, and a radiation shield 34 disposed in the beam shaping assembly 30. The neutron beam generating unit T and the charged particle beam P emitted from the charged particle beam inlet perform a nuclear reaction to generate the neutron beam N. The neutron beam defines a principal axis, the moderator 32 moderates neutrons generated by the neutron beam generating unit T to an epithermal neutron energy region, the reflector 31 guides the neutrons deviating from the principal axis back to the principal axis so as to improve the intensity of an epithermal neutron beam, the thermal neutron absorber 33 is used for absorbing thermal neutrons so as to avoid excess doses caused with normal tissues of a superficial layer during therapy, and the radiation shield 34 is used for shielding leaked neutrons and photons so as to reduce a normal tissue dose of a non-irradiation region. The beam outlet 40 may also be referred to as a neutron beam convergence part or a collimator, which reduces the widths of neutron beams so as to gather the neutron beams. The neutron beams emitted from the beam outlet 40 irradiate a target part of the irradiated body 50.

The beam diagnostic system includes a charged particle beam diagnostic device and a neutron beam diagnostic device, and the beam diagnostic system is used for simultaneously diagnosing whether the neutron capture therapy system and/or the beam diagnostic system is malfunctioning. The beam diagnostic system improves the accuracy of a neutron beam irradiation dose by detecting the charged particle beam and the neutron beam simultaneously. In addition, the beam diagnostic system is used for judging which devices and/or components in the neutron capture therapy system are abnormal by means of a series of detection results, or judging whether a detection device in the beam diagnostic system is abnormal. Thus, not only the accuracy of the neutron beam irradiation dose is improved with a purpose, but also the maintenance time and cost are greatly reduced.

The charged particle beam diagnostic device further includes a first current detection device 100 for detecting the intensity and stability of the charged particle beam P before entering the charged particle beam inlet, and a second current detection device 200 for detecting the intensity and change situation of the charged particle beam P interacting with the neutron beam generating unit T; the beam diagnostic system further includes a temperature detection device 300 for detecting the temperature of the cooling device 60 so as to obtain a situation of the cooling device 60 and the neutron beam N generating of the neutron beam generating unit T; the neutron beam diagnostic device further includes a first neutron beam monitoring device 400 which is used for detecting the intensity change and space distribution of the neutron beam N in the beam shaping assembly 30 and is embedded in the beam shaping assembly 30, and a second neutron beam monitoring device 500 which is used for detecting the intensity change and space distribution of the neutron beam N at the beam outlet 40 and is embedded at the beam outlet 40; and the beam diagnostic system further includes a displacement detection device 600 for diagnosing whether the irradiated body 50 displaces. The first neutron beam monitoring device 400 may be provided with two neutron beam monitoring members namely a first neutron beam monitoring member 401 and a second neutron beam monitoring member 402; the second neutron beam monitoring device 500 may be provided with two neutron beam monitoring members namely a third neutron beam monitoring member 501 and a fourth neutron beam monitoring member 502; and the displacement detection device 600 may be provided with two displacement detection members namely a first displacement detection member 601 and a second displacement detection member 602.

Although in the subject disclosure, the first neutron beam monitoring device 400, the second neutron beam monitoring device 500 and the displacement detection device 600 are provided with two respective monitoring/detection members separately, it is well known to a person skilled in the art that the number of the monitoring/detection members may be set as required. For example, there may be four, six or eight monitoring/detection members. As long as a neutron beam monitoring member is embedded into the beam shaping assembly (or near the beam shaping assembly) and/or in the beam outlet (or near the beam outlet) and can be used for detecting the intensity change and space distribution of the neutron beam, the neutron beam monitoring member may be selected for use. As long as a displacement detection member is disposed in the irradiated body (or near the irradiated body) and can be used for detecting the displacement change of the irradiated body, the displacement detection member may be selected for use. In addition, the placement positions of the monitoring/detection members are not strictly limited. It is only required to make the placement positions able to achieve corresponding detection functions.

By means of such setting, various detection devices are disposed from the source of the accelerator to the terminal of the irradiated body. The detection devices are used for judging whether each key component of the neutron capture therapy system or the detection devices themselves are abnormal. The detection devices may be disposed from the source of the accelerator to the terminal of the irradiated body in such a way that a detection device is disposed at a vacuum tube at the source of the accelerator, a detection device is disposed at the neutron beam generating unit, a detection device is disposed at the cooling device which abuts the neutron beam generating unit and is used for cooling the neutron beam generating unit, a detection device is disposed in the beam shaping assembly, a detection device is disposed at the beam outlet, and a detection device is disposed at the irradiated body.

In the subject disclosure, the first current detection device 100 is a Faraday cup electrometer, which is a cup-shaped metal vacuum detector for measuring the incident intensity and stability of the charged particle beam, wherein a measured current may be used for determining the quantity of charged particle beams. When the charged particle beam enters the Faraday cup electrometer, a current will be generated. A successive charged particle beam with a single charge is calculated by means of FORMULA 1, where N is the quantity of charged particles, t is time (in second), I is a measured current (in ampere), and e is an elementary charge (about $1.60 \times 10^{-19}$ coulombs). It is estimable that if the measured current is $10^{-9}$ A (1 nA), about six billion charged particles are collected by the Faraday cup electrometer.

$$\frac{N}{t} = \frac{I}{e} \quad \text{(FORMULA 1)}$$

Certainly, it is well known to a person skilled in the art that the first current detection device 100 may be any detection device suitable for measuring the incident intensity and stability of the charged particle beam at the vacuum tube of the accelerator, such as a wall current monitor and a beam current transformer.

The wall current monitor bridges sampling resistors to two ends of a ceramic isolation segment, a voltage sampling signal can be obtained when a beam mirror current flows through the sampling resistors, and the voltage sampling signal is calculated by means of FORMULA 2, where V is a detected voltage value, $I_b$ is a charged particle beam current, Z may be equivalent to resistance under a specific frequency, and a wall current monitor equivalent circuit is a parallel RLC circuit, as shown in FORMULA 3. Therefore, the current of the charged particle beam within a certain period of time t can be calculated according to the detected voltage value.

$$V = -I_b(t) Z \quad \text{(FORMULA 2)}$$

$$\frac{1}{Z} = \frac{1}{R} + \frac{1}{j\omega L} + j\omega C \quad \text{(FORMULA 3)}$$

The beam current transformer is used for coupling a current signal by utilizing a secondary winding on a magnetic core to obtain the current of an original charged particle beam by analyzing the signal, such as AC Current Transformer (ACCT), Fast Current Transformer (FCT), Tuned Current Transformer (TCT), Integrated Current Transformer (ICT) and DC Current Transformer (DCCT). Due to numerous varieties, the beam current transformers will not be enumerated one by one hereinafter. Only the DCCT is taken as an example. The DCCT modulates a DC signal to be detected to secondary harmonics of an excitation signal for detection by adopting a nonlinear magnetic modulation component.

In the subject disclosure, the second current detection device 200 is a galvanometer, one end being electrically connected to the neutron beam generating unit T and the other one being grounded, so as to form a detection loop, thereby obtaining a current on the neutron beam generating unit T when the charged particle beam P bombards the neutron beam generating unit T. The galvanometer is made according to a principle that a current-carrying coil deflects in a magnetic field under the action of torque. A coil in a common electric meter is placed on a bearing, keeps balanced by using a balance spring, and the deflection is indicated by a pointer. The bearing is frictional, so the measured current cannot be too weak. In the galvanometer, a very thin metal suspension wire instead of the bearing is suspended in the magnetic field. The suspension wire is thin and long, and a resisting torque is small, so the coil can be obviously deflected when a very weak current passes through the coil. Thus, the galvanometer is more sensitive than a common electric meter, and can measure a micro-current ($10^{-7}$-$10^{-10}$ A) or a micro-voltage ($10^{-3}$-$10^{-6}$V) such as a light current, a physiological current and a thermal electromotive force. The first record about a nerve action potential was made by using this type of instrument.

Certainly, it is well known to a person skilled in the art that the second current detection device 200 may be any detection device suitable for detecting, near the neutron beam generating unit, the intensity and change situations of the charged particle beam interacting with the neutron beam generating unit, such as an electric meter and a voltmeter.

In the subject disclosure, the temperature detection device 300 is a thermocouple. Both ends of two conductors (referred to as thermocouple wires or thermal electrodes) with different components are connected into a loop. When the temperatures of junctions are different, an electromotive force will be generated in the loop, the phenomenon is referred to as a thermo-electric effect, the electromotive force is referred to as a thermal electromotive force. The thermocouple performs temperature measurement by utilizing the principle, wherein an end directly used for measuring a medium temperature is referred to as a working end (or measurement end) whilst the other end is referred to as a cold end (or compensation end). The cold end is connected with a display instrument or an auxiliary instrument, and the display instrument will indicate the thermal electromotive force generated by the thermocouple.

Certainly, it is well known to a person skilled in the art that the temperature detection device 300 may be any detection device suitable for being disposed in the cooling device or near the cooling device and used for detecting the temperature of the cooling device so as to obtain a situation of the cooling device and the neutron beam generating of the neutron beam generating unit, such as a resistance thermometer, which measures a temperature according to a rule of varying of conductor resistance along with temperature by using a temperature sensor made of a material characterized by varying of given resistance along with temperature.

A common neutron beam monitoring device for real-time detection may have two different detection principles, namely an ionization chamber and a scintillator detector. Those adopting ionization chamber structures as substrates include He-3 proportional counter, $BF_3$ proportional counter, fission chamber and boron ionization chamber. The scintillator detector may be divided into organic and inorganic materials, and for the purpose of detecting thermal neutrons, the scintillator detector mainly adds high thermal neutron capture section elements such as Li or B. In short, most of neutron energies detected by this type of detectors are the thermal neutrons, which all rely on heavy charged particles and nuclear fission fragments released by means of a capture or nuclear fission reaction between elements and neutrons, a great number of ion pairs are generated in the ionization chamber or the scintillator detector, and after the charges are collected, a current signal may be converted into a voltage pulse signal via appropriate circuit conversion. A neutron signal and a γ signal can be easily distinguished from each other by analyzing the magnitude of a voltage pulse. In a high-intensity neutron field such as a BNCT, the gas pressure of the ionization chamber, the concentration of coating of fissionable materials or boron or the concentration of the high neutron capture section elements in the scintillator detector can be appropriately reduced, so the sensitivity to neutrons can be effectively reduced, and the situation of signal saturation is avoided.

The first neutron beam monitoring device 400 may be a fission chamber. When passing through the fission chamber, a neutron beam ionizes gas molecules inside the fission chamber or a wall portion of the fission chamber to generate an electron and an ion with a positive charge, the electron and the positive charge ion are referred to as the aforementioned ion pair. The interior of the fission chamber has an external electric field high voltage, so the electron moves toward a central anode wire, and the positive charge ion moves toward a surrounding cathode wall, thus generating an electronic pulse signal which can be measured. An energy needed for generating an ion pair by gas molecules is referred to as an average ionizing energy, the value varying with a gas type. For example, the average ionizing energy of air is about 34 eV. If a neutron beam of 340 keV exists, the air will generate about 10 k ion pairs.

Certainly, it is well known to a person skilled in the art that the first neutron beam monitoring device 400 may be any detection device suitable for being embedded in the beam shaping assembly and used for detecting the intensity change and space distribution of the neutron beam in the beam shaping assembly, such as He-3 proportional counter, BF3 proportional counter, boron ionization chamber and scintillator detector.

The second neutron beam monitoring device 500 may be a scintillator detector, and after certain materials absorbing energy, visible light will be emitted, and the materials are referred to as scintillating materials. It utilizes ionizing radiation to excite an electron in a crystal or molecule to an exciting state, fluorescent light emitted when the electron returns to a base state is used for monitoring a neutron beam after being collected. The visible light emitted after the scintillator detector interacts with the neutron beam can be converted into an electron by utilizing a photomultiplier, and the electron is multiplied and amplified, wherein the multiplication and amplification rate of the electron can reach 107 to 108 usually. The quantity of electrons output from an anode is in direct proportion to energy of an incident neutron beam, and therefore the scintillator detector can measure the energy of the neutron beam.

Certainly, it is well known to a person skilled in the art that the second neutron beam monitoring device 500 may be any detection device suitable for being disposed in the beam outlet or near the beam outlet and used for detecting the intensity change and space distribution of a neutron beam at the beam outlet, such as He-3 proportional counter, $BF_3$ proportional counter, boron ionization chamber and fission chamber.

The displacement detection device 600 may be an infrared signal detector, the infrared detector works by detecting an infrared ray emitted by a human body. The detector collects external infrared radiation and further gathers the external infrared radiation to an infrared sensor. The infrared sensor usually adopts a pyroelectric element. The element will release a charge outward after receiving an infrared radiation temperature change, and will give an alarm after detection. The detector aims to detect human body radiation. A radiation-sensitive element must be very sensitive to infrared radiation of which a wavelength is about 10 μm.

Certainly, it is well known to a person skilled in the art that the displacement detection device 600 may be any detection device suitable for being used for detecting the displacement change of the irradiated body, such as a displacement sensor. The displacement sensor determines whether the irradiated body moves according to the displacement change of the irradiated body relative to a certain reference substance. It is also well known to a person skilled in the art that the displacement detection device not only can be used for detecting the displacement change of the irradiated body, but also can be used for detecting the displacement change of a supporting piece for fixing the irradiated body and/or a therapy table, thereby indirectly knowing the displacement change of the irradiated body.

It is well known to a person skilled in the art that the number of first current detection devices, the number of second current detection devices, the number of temperature detection devices, the number of first neutron beam monitoring devices, the number of second neutron beam monitoring devices, the number of displacement detection devices, and detection elements are not limited. The numbers and the detection elements in the subject disclosure are only taken as an example.

According to a function relationship between detection results of detection and/or monitoring devices, malfunctioning components can be obviously enumerated. Several fault diagnosis situations made according to corresponding detection results will be enumerated hereinafter.

When it is detected that any one detection or monitoring device of the first current detection device 100, the second current detection device 200, the temperature detection device 300, the first neutron beam monitoring device 400 and the second neutron beam monitoring device 500 is abnormal whilst all other detection or monitoring devices are normal, it is concluded that the abnormal detection or monitoring device itself is malfunctioning; and when it is detected that the displacement detection device 600 is abnormal whilst all other detection or monitoring devices are normal, it is concluded that the displacement of the irradiated body 50 is changed or the displacement detection device 600 is malfunctioning.

When it is detected that the first current detection device 100, the second current detection device 200, the temperature detection device 300, the first neutron beam monitoring device 400 and the second neutron beam monitoring device 500 are all abnormal, it is concluded that the accelerator 10 is malfunctioning.

When it is detected that the second current detection device 200, the temperature detection device 300, the first neutron beam monitoring device 400 and the second neutron beam monitoring device 500 are all abnormal whilst both the first current detection device 100 and the displacement detection device 600 are normal, it is concluded that the beam expanding device 20 is malfunctioning.

When it is detected that the temperature detection device 300, the first neutron beam monitoring device 400 and the second neutron beam monitoring device 500 are all abnormal whilst the first current detection device 100, the second current detection device 200 and the displacement detection device 600 are all normal, it is concluded that the neutron beam generating unit T and/or the cooling device 60 is malfunctioning.

When it is detected that both the first neutron beam monitoring device 400 and the second neutron beam monitoring device 500 are abnormal whilst the first current detection device 100, the second current detection device 200, the temperature detection device 300 and the displacement detection device 600 are all normal, it is concluded that the beam shaping assembly 30 is malfunctioning.

When it is detected that any one of monitoring results of the first neutron beam monitoring member 401 and the second neutron beam monitoring member 402 and/or any one of the third neutron beam monitoring member 501 and the fourth neutron beam monitoring member 502 is abnormal, it is concluded that the abnormal neutron beam monitoring member itself is malfunctioning or the uniformity of the neutron beam is abnormal.

Certainly, it is well known to a person skilled in the art that the aforementioned fault diagnosis situations made according to the detection results are only some enumerated common situations, there are many permutations and combinations, and the above modes can be still adopted to judge which neutron capture therapy systems or detection devices are malfunctioning and which faults are included. Here, although they are not enumerated one by one, changes made according to such a spirit still fall within the summary of the present disclosure.

The beam diagnostic system includes a control device 700 with a control unit 710, the control unit 710 sends a human-perceivable signal according to a detection result of the beam diagnostic system so as to confirm a next operation of the neutron capture therapy system. The human-perceivable signal may be a signal which can be perceived by human functional organs such as auditory sense, visual sense, tactile sense or smell sense. For example, the signal is one or more forms in various signals such as a sound-making alarm, an alarm lamp, a vibrating signal and a pungent smell emitting signal. The control device 700 may further includes a display unit 720, the display unit 720 is used for displaying a detection result of the detection device and/or a fault diagnosis situation made according to the detection result on display equipment, and the display equipment may be common display equipment such as a television or a liquid crystal display. According to a feedback from the control device, an operator can easily determine a malfunctioning component, thereby maintaining the neutron capture therapy system and/or the beam diagnostic system with a purpose.

Figure 5:
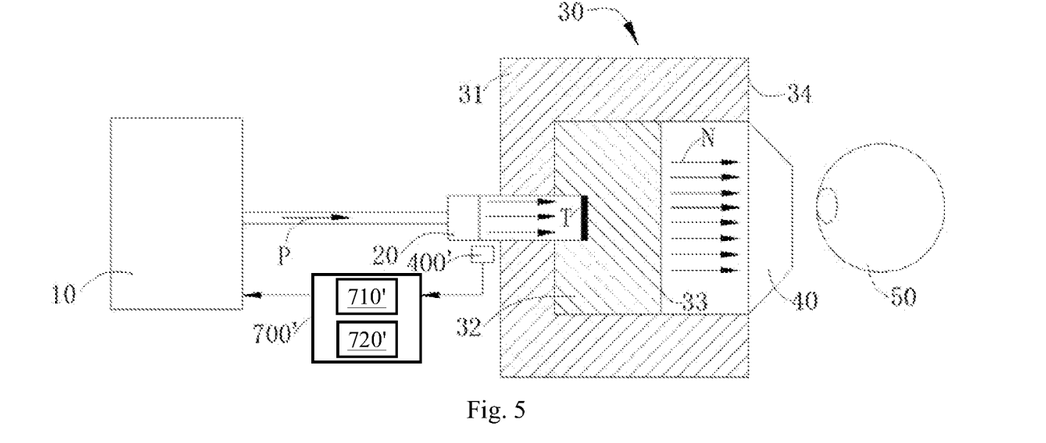
FIG. 5 is a schematic view of the first neutron beam monitoring device of the beam diagnostic system in another embodiment of the present disclosure.

Further referring to FIG. 5, it shows another embodiment of the first neutron beam monitoring device. The first neutron beam monitoring device is marked by number 400', the devices/members as shown in the figure, which are identical to those in FIG. 3, are still marked by the same numeric identifiers, and for convenience of display, the cooling device and other monitoring/detection devices are omitted.

The first neutron beam monitoring device 400' may include one or more neutron beam monitoring members, it can be disposed near the beam shaping assembly 30 to detect a neutron beam overflowing through the neutron beam generating unit T so as to detect the intensity change and space distribution of the neutron beam in a direct manner, and can also be disposed near the beam shaping assembly 30 to detect a γ ray generated by interaction between the charged particle beam P and the neutron beam generating unit T. The intensity change and space distribution of the neutron beam can be indirectly detected according to a function relationship between the γ ray and the neutron beam. The control device 700' includes a control unit 710' and a display unit 720'. The display unit 720' is used for displaying a detection result of a detection device 400' and/or a fault diagnosis situation made according to the detection result on display equipment, and the display equipment may be common display equipment such as a television or a liquid crystal display. According to a feedback from the control device, an operator can easily determine a malfunctioning component, thereby executing a next operation on the accelerator 10 with a purpose.

To sum up, it is not limited whether the first neutron beam monitoring device is disposed in the beam shaping assembly or near the beam shaping assembly, and any detection device which can be used for detecting the intensity change and space distribution of the neutron beam in the beam shaping assembly at the arrangement position may be selected.

The beam diagnostic system for the neutron capture therapy system disclosed by the present disclosure is not limited to the contents in the foregoing embodiments and the structures shown in the drawings. All obvious changes, replacements or modifications made on materials, shapes and positions of members on the basis of the present disclosure fall within the scope of protection of the present disclosure.

What is claimed is:

1. A beam diagnostic system for a neutron capture therapy system, the beam diagnostic system comprising:
    a charged particle beam diagnostic device; and
    a neutron beam diagnostic device,
    wherein the neutron capture therapy system comprises:
        a charged particle beam;
        a charged particle beam inlet for passing the charged particle beam;
        a neutron beam generating unit for generating the neutron beam by a nuclear reaction with the charged particle beam;
        a beam shaping assembly for adjusting flux and quality of the neutron beam generated by the neutron beam generating unit; and
        a beam outlet adjoining to the beam shaping assembly,
    wherein the charged particle beam diagnostic device and the neutron beam diagnostic device are used to simultaneously diagnose whether the neutron capture therapy system and/or the beam diagnostic system is malfunctioning.

2. The beam diagnostic system according to claim 1, wherein the neutron capture therapy system further comprises a cooling device arranged into the neutron beam generating unit for cooling the neutron beam generating unit, and the beam diagnostic system further comprises a temperature detection device for detecting the temperature of the cooling device so as to obtain a status of the neutron beam generated by the neutron generating unit and a displacement detection device for diagnosing whether an irradiated body displaces.

3. The beam diagnostic system according to claim 2, wherein the neutron capture therapy system further comprises a beam expanding device for expanding the charged particle beam; the charged particle beam diagnostic device further comprises a first current detection device for detecting intensity and stability of the charged particle beam before entering the charged particle beam inlet and a second current detection device for detecting intensity and change status of the charged particle beam interacting with the neutron generating unit; and the neutron beam diagnostic device further comprises a first neutron beam monitoring device which is used for detecting intensity change and space distribution of the neutron beam in the beam shaping assembly and is embedded into the beam shaping assembly, and a second neutron beam monitoring device which is used for detecting the intensity change and space distribution of the neutron beam at the beam outlet and is embedded at the beam outlet.

4. The beam diagnostic system according to claim 3, wherein when it is detected that any one device of the first current detection device, the second current detection device, the temperature detection device, the first neutron beam monitoring device and the second neutron beam monitoring device is abnormal whilst all other of the first current detection device, the second current detection device, the temperature detection device, the first neutron beam monitoring device and the second neutron beam monitoring device are normal, it is concluded that the abnormal device is malfunctioning; and when it is detected that the displacement detection device is abnormal whilst all other of the first current detection device, the second current detection device, the temperature detection device, the first neutron beam monitoring device and the second neutron beam monitoring device are normal, it is concluded that the displacement of the irradiated body is changed or the displacement detection device is malfunctioning.

5. The beam diagnostic system according to claim 3, wherein the neutron capture therapy system further comprises an accelerator for accelerating the charged particle beam, and when it is detected that the first current detection device, the second current detection device, the temperature detection device, the first neutron beam monitoring device and the second neutron beam monitoring device are all abnormal, it is concluded that the accelerator is malfunctioning.

6. The beam diagnostic system according to claim 3, wherein when it is detected that the second current detection device, the temperature detection device, the first neutron beam monitoring device and the second neutron beam monitoring device are all abnormal whilst both the first current detection device and the displacement detection device are normal, it is concluded that the beam expanding device is malfunctioning.

7. The beam diagnostic system according to claim 3, wherein when it is detected that the temperature detection device, the first neutron beam monitoring device and the second neutron beam monitoring device are all abnormal whilst the first current detection device, the second current detection device and the displacement detection device are all normal, it is concluded that the neutron generating unit and/or the cooling device is malfunctioning.

8. The beam diagnostic system according to claim 3, wherein when it is detected that both the first neutron beam monitoring device and the second neutron beam monitoring device are abnormal whilst the first current detection device, the second current detection device, the temperature detection device and the displacement detection device are all normal, it is concluded that the beam shaping assembly is malfunctioning.

9. The beam diagnostic system according to claim 3, wherein the first neutron beam monitoring device comprises a first neutron beam monitoring member and a second neutron beam monitoring member which are located at two opposite sides in the beam shaping assembly respectively, the second neutron beam monitoring device comprises a third neutron beam monitoring member and a fourth neutron beam monitoring member which are located at two opposite sides of the beam outlet respectively, and when it is detected that any one of monitoring results of the first neutron beam monitoring member and the second neutron beam monitoring member and/or any one of the third neutron beam monitoring member and the fourth neutron beam monitoring member is abnormal, it is concluded that the abnormal neutron beam monitoring member is malfunctioning or the uniformity of the neutron beam is abnormal.

10. The beam diagnostic system according to claim 1, wherein the beam diagnostic system comprises a control device with a control unit, wherein the control unit sends a human-perceivable signal according to a detection result of the beam diagnostic system so as to confirm a next operation of the neutron capture therapy system.

11. A beam diagnostic system for a neutron capture therapy system, the beam diagnostic system comprising:
a charged particle beam diagnostic device; and
a neutron beam diagnostic device,
wherein the neutron capture therapy system comprises:
a charged particle beam;
a charged particle beam inlet for passing the charged particle beam;
a neutron beam generating unit for generating the neutron beam by a nuclear reaction with the charged particle beam;
a beam shaping assembly for adjusting flux and quality of the neutron beam generated by the neutron beam generating unit; and
a beam outlet adjoining to the beam shaping assembly,
wherein the charged particle beam diagnostic device and the neutron beam diagnostic device are used to simultaneously diagnose whether the neutron capture therapy system and/or the beam diagnostic system is malfunctioning;
wherein the neutron beam diagnostic device further comprises a first neutron beam monitoring device which is used for detecting intensity change and space distribution of the neutron beam in the beam shaping assembly and is embedded into the beam shaping assembly, and a second neutron beam monitoring device which is used for detecting intensity change and space distribution of the neutron beam at the beam outlet and is embedded at the beam outlet; and
wherein the charged particle beam diagnostic device, the first neutron beam monitoring device and the second neutron beam monitoring device are used to simultaneously diagnose whether the neutron capture therapy system and/or the beam diagnostic system is malfunctioning.

12. The beam diagnostic system according to claim 11, wherein the neutron capture therapy system further comprises a cooling device arranged into the neutron beam generating unit for cooling the neutron beam generating unit, and the beam diagnostic system further comprises a temperature detection device for detecting the temperature of the cooling device so as to obtain a status of the neutron beam generated by the neutron generating unit and a displacement detection device for diagnosing whether an irradiated body displaces.

13. The beam diagnostic system according to claim 12, wherein the neutron capture therapy system further comprises a beam expanding device for expanding the charged particle beam.

14. The beam diagnostic system according to claim 11, wherein the charged particle beam diagnostic device further comprises a first current detection device for detecting intensity and stability of the charged particle beam before entering the charged particle beam inlet and a second current detection device for detecting intensity and change status of the charged particle beam interacting with the neutron generating unit.

15. The beam diagnostic system according to claim 11, wherein the beam diagnostic system comprises a control device with a control unit, wherein the control unit sends a human-perceivable signal according to a detection result of the beam diagnostic system so as to confirm a next operation of the neutron capture therapy system.

16. A beam diagnostic system for a neutron capture therapy system, the beam diagnostic system comprising:
a charged particle beam diagnostic device; and
a neutron beam diagnostic device,
wherein the neutron capture therapy system comprises:
a charged particle beam;
a charged particle beam inlet for passing the charged particle beam;
a neutron beam generating unit for generating the neutron beam by a nuclear reaction with the charged particle beam;
a beam shaping assembly for adjusting flux and quality of the neutron beam generated by the neutron beam generating unit; and
a beam outlet adjoining to the beam shaping assembly,
wherein the charged particle beam diagnostic device and the neutron beam diagnostic device are used to simultaneously diagnose whether the neutron capture therapy system and/or the beam diagnostic system is malfunctioning;
wherein the charged particle beam diagnostic device further comprises a first current detection device for detecting intensity and stability of the charged particle beam before entering the charged particle beam inlet and a second current detection device for detecting intensity and change status of the charged particle beam interacting with the neutron generating unit; and
wherein the first current detection device, the second current detection device and the neutron beam diagnostic device is used to simultaneously diagnose whether the neutron capture therapy system and/or the beam diagnostic system is malfunctioning.

17. The beam diagnostic system according to claim 16, wherein the neutron capture therapy system further comprises a cooling device arranged into the neutron beam generating unit for cooling the neutron beam generating unit, and the beam diagnostic system further comprises a temperature detection device for detecting the temperature of the cooling device so as to obtain a status of the neutron beam generated by the neutron generating unit and a displacement detection device for diagnosing whether an irradiated body displaces.

18. The beam diagnostic system according to claim 17, wherein the neutron capture therapy system further comprises a beam expanding device for expanding the charged particle beam.

19. The beam diagnostic system according to claim 16, wherein the neutron beam diagnostic device further comprises a first neutron beam monitoring device which is used for detecting intensity change and space distribution of the neutron beam in the beam shaping assembly and is embedded into the beam shaping assembly, and a second neutron beam monitoring device which is used for detecting intensity change and space distribution of the neutron beam at the beam outlet and is embedded at the beam outlet.

20. The beam diagnostic system according to claim 16, wherein the beam diagnostic system comprises a control device with a control unit, wherein the control unit sends a human-perceivable signal according to a detection result of the beam diagnostic system so as to confirm a next operation of the neutron capture therapy system.

* * * * *